US012082927B2

(12) United States Patent
Lin et al.

(10) Patent No.: US 12,082,927 B2
(45) Date of Patent: Sep. 10, 2024

(54) TOPICAL SUBCUTANEOUS MICROCIRCULATION DETECTION DEVICE

(71) Applicant: Chung Yuan Christian University, Taoyuan (TW)

(72) Inventors: Kang-Ping Lin, Taoyuan (TW); Cheng Lun Tsai, Taoyuan (TW); Shao-Hung Lu, Taoyuan (TW); Mei-Fen Chen, Taoyuan (TW)

(73) Assignee: Chung Yuan Christian University, Taoyuan (TW)

( * ) Notice: Subject to any disclaimer, the term of this patent is extended or adjusted under 35 U.S.C. 154(b) by 442 days.

(21) Appl. No.: 17/502,045

(22) Filed: Oct. 15, 2021

(65) Prior Publication Data

US 2022/0133188 A1 May 5, 2022

(30) Foreign Application Priority Data

Oct. 29, 2020 (TW) .................... 109137545

(51) Int. Cl.
*A61B 5/1455* (2006.01)
*A61B 5/00* (2006.01)

(52) U.S. Cl.
CPC ........ *A61B 5/14552* (2013.01); *A61B 5/0059* (2013.01); *A61B 5/445* (2013.01)

(58) Field of Classification Search
CPC ... A61B 5/14552; A61B 5/0059; A61B 5/445; A61B 5/0205; A61B 5/1455; A61B 5/14551; A61B 5/14553; A61B 5/14556; A61B 5/1464; A61B 5/14532; A61B 5/14535; A61B 5/14539; A61B 5/14542; A61B 5/14546

See application file for complete search history.

(56) References Cited

U.S. PATENT DOCUMENTS

| 6,223,063 | B1* | 4/2001 | Chaiken ............. A61B 5/14552 600/335 |
| 8,116,838 | B2 | 2/2012 | Gaspard et al. |
| 8,352,003 | B2* | 1/2013 | Sawada ............... A61B 5/0261 600/324 |
| 2010/0085537 | A1 | 4/2010 | Ramella-Roman et al. |

FOREIGN PATENT DOCUMENTS

| TW | M451943 | 5/2013 |
| TW | 201536255 | 10/2015 |
| TW | 201542161 | 11/2015 |
| WO | 2016031221 | 3/2016 |

* cited by examiner

*Primary Examiner* — Chu Chuan Liu

(74) *Attorney, Agent, or Firm* — JCIPRNET

(57) ABSTRACT

A topical subcutaneous microcirculation detection device includes a first light source module, a second light source module, a lens plate, a first light sensor, and a second light sensor. The first and second light source modules are configured to emit first and second illumination beams, respectively. A flat plate portion of the lens plate is disposed to lean against a first portion of skin of a subject. A convex surface of a first convex lens portion of the lens plate is disposed to push into a second portion of the skin of the subject. The first and second illumination beams are reflected into first and second reflected beams by the first and second portions of the skin, respectively. The first and second reflected beams are transmitted to the first and second light sensors, respectively.

15 Claims, 3 Drawing Sheets

TOPICAL SUBCUTANEOUS MICROCIRCULATION DETECTION DEVICE

CROSS-REFERENCE TO RELATED APPLICATION

This application claims the priority benefit of Taiwan application serial no. 109137545, filed on Oct. 29, 2020. The entirety of the above-mentioned patent application is hereby incorporated by reference herein and made a part of this specification.

BACKGROUND

Technical Field

The disclosure relates to an optical detection device, and in particular, to a topical subcutaneous microcirculation detection device.

Description of Related Art

Pressure injuries are a common skin disease for long-term bedridden patients. The skin disease mainly results from long-term stress placed on the skin, which leads to vascular skin lesions and eventually results in open wounds.

In the early stage of the disease, the compressed blood vessels produce lesions, and the ability to supply skin tissue nutrients and take away waste products generated after metabolism is decreased. As a result, skin tissue necrosis occurs over time. Open wounds resulting from the skin tissue necrosis may make it increasingly difficult for caring the patients and may also increase the mortality of patients, resulting in a substantial increase in family expenditure and the cost of caring.

Currently, "skin blanching test" is one of the most reliable clinical test methods to identify early pressure injuries, which are mainly determined by observing the amount of the blood flow that returns after professional caregivers press the skin. However, the clinical skin blanching test cannot be applied to the field of home care, and for patients with dark skin, it is difficult to observe the blanching of the skin with naked eyes. Moreover, even if the skin blanching test is performed by a professional caregiver, it is still visually observed and judged based on the experience, and it is impossible to make a quantitative measurement.

SUMMARY

The disclosure provides a topical subcutaneous microcirculation detection device capable of quantitatively measuring topical subcutaneous microcirculation of a subject.

An embodiment of the disclosure provides a topical subcutaneous microcirculation detection device, which includes a first light source module, a second light source module, a lens plate, a first light sensor, and a second light sensor. The first light source module is configured to emit a first illumination beam. The second light source module is configured to emit a second illumination beam. The lens plate includes a flat plate portion and a first convex lens portion. The flat plate portion is configured to lean against a first portion of skin of a subject. A convex surface of the first convex lens portion is configured to press into a second portion of the skin of the subject. The first illumination beam penetrates the flat plate portion and is then reflected by the first portion of the skin into a first reflected beam, and the second illumination beam penetrates the first convex lens portion and is then reflected by the second portion of the skin into a second reflected beam. The first reflected beam penetrates the flat plate portion and is then transmitted to the first light sensor. The second reflected beam penetrates the first convex lens portion and is then transmitted to the second light sensor.

An embodiment of the disclosure provides a topical subcutaneous microcirculation detection device, which includes a light reflecting housing, a first light source module, a second light source module, a lens plate, a first light sensor, and a second light source module. The light reflecting housing includes a first light integration space and a second light integration space separated from each other. The first light source module is disposed in the first light integration space and configured to emit a first illumination beam transmitted in the first light integration space. The second light source module is disposed in the second light integration space and configured to emit a second illumination beam transmitted in the second light integration space. The lens plate includes a flat plate portion and a first convex lens portion, respectively disposed at one end of the first light integration space and one end of the second light integration space. The flat plate portion is configured to lean against a first portion of skin of a subject, a convex surface of the first convex lens portion is configured to press into a second portion of the skin of a subject, the first illumination beam penetrates the flat plate portion and is then reflected by the first portion of the skin into a first reflected beam, and the second illumination beam penetrates the first convex lens portion and is then reflected by the second portion of the skin into a second reflected beam. The first reflected beam penetrates the flat plate portion and is then transmitted to the first light sensor through the first light integration space. The second reflected beam penetrates the first convex lens portion and is then transmitted to the second light sensor through the second light integration space.

In the topical subcutaneous microcirculation detection device of the embodiments of the disclosure, the lens plate having a flat plate portion and a first convex lens portion is configured to perform actions of no pressing and pressing on the skin, and the first light source module, the first light sensor, the second light source module, and the second light sensor are used for optical detection of the skin that is not pressed and the skin that is pressed, respectively. Accordingly, in the topical subcutaneous microcirculation detection device of the embodiments of the disclosure, a quantitative measurement of the topical subcutaneous microcirculation of subjects can be implemented.

DESCRIPTION OF THE EMBODIMENTS

Figure 1:
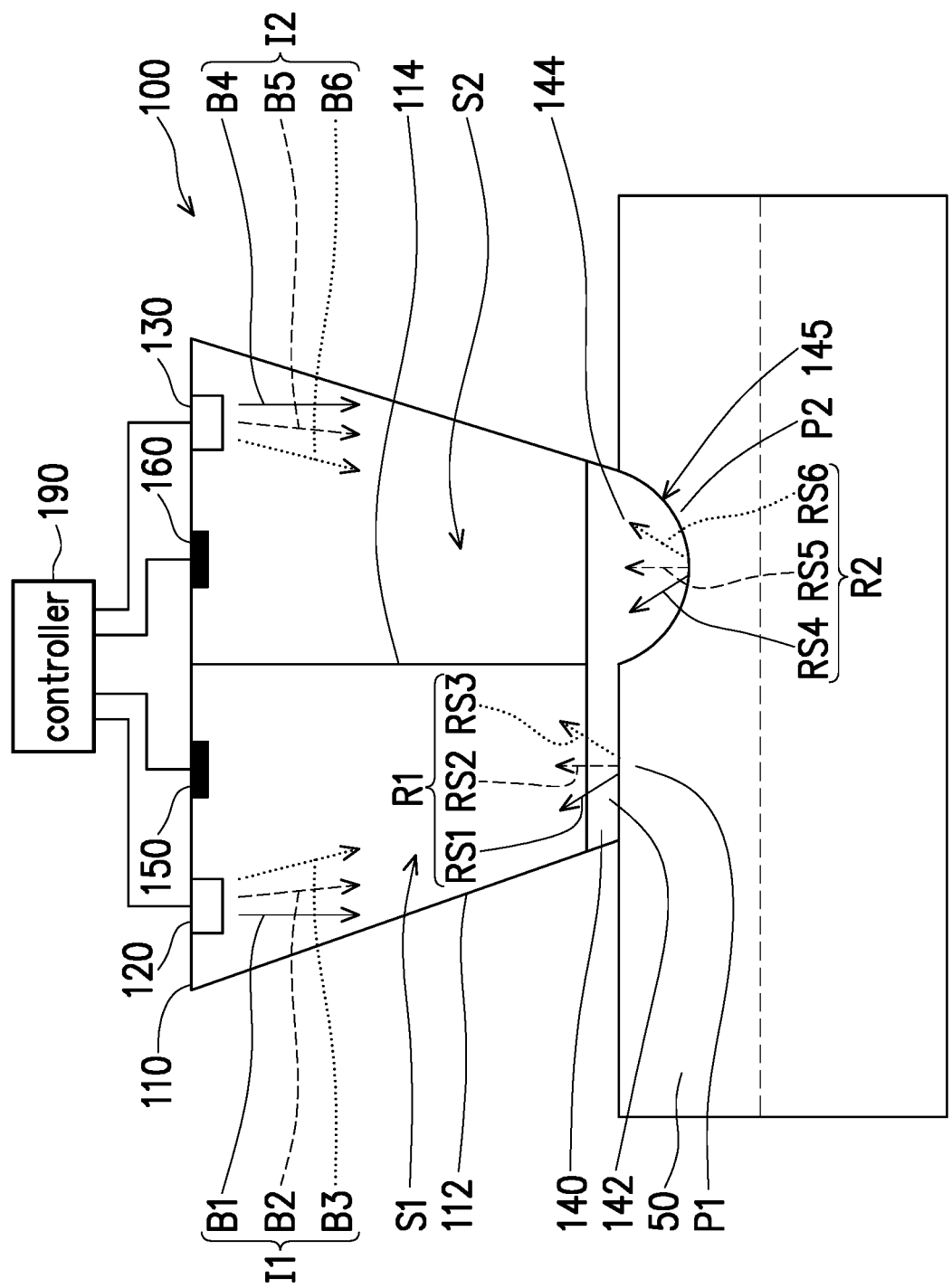
FIG. 1 is a schematic cross-sectional view of a topical subcutaneous microcirculation detection device according to an embodiment of the disclosure.
Figure 2:
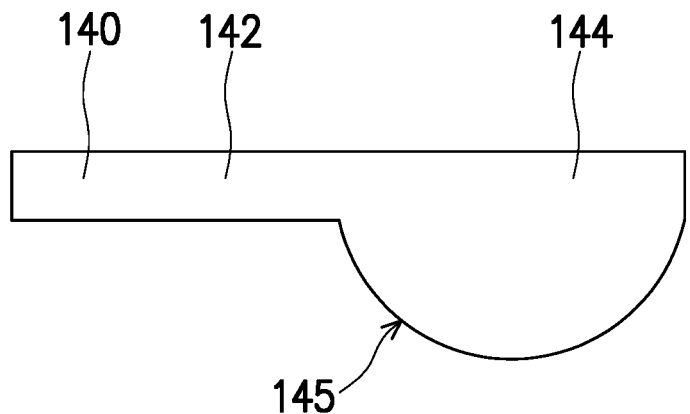
FIG. 2 is a schematic cross-sectional view of a lens plate in FIG. 1.
Figure 3:
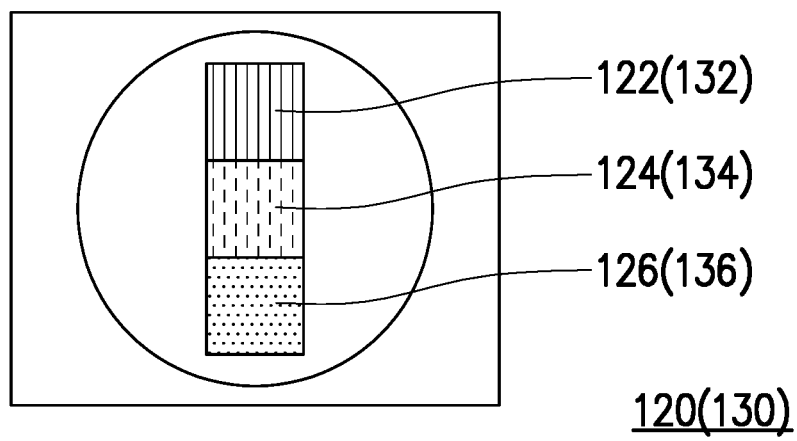
FIG. 3 is a schematic front view of a light source module in FIG. 1.

FIG. 1 is a schematic cross-sectional view of a topical subcutaneous microcirculation detection device according to an embodiment of the disclosure, FIG. 2 is a schematic cross-sectional view of a lens plate in FIG. 1, and FIG. 3 is a schematic front view of a light source module in FIG. 1. Referring to FIG. 1, FIG. 2, and FIG. 3, a topical subcutaneous microcirculation detection device 100 of the embodiment includes a light reflecting housing 110, a first light source module 120, a second light source module 130, a lens plate 140, a first light sensor 150, and a second light sensor 160. The light reflecting housing 110 has a first light integration space S1 and a second light integration space S2 separated from each other. The first light source module 120 is disposed in the first light integration space S1 and configured to emit a first illumination beam I1 transmitted in the first light integration space S1. The second light source module 130 is disposed in the second light integration space S2 and configured to emit a second illumination beam I2 transmitted in the second light integration space S2. In the embodiment, the light reflecting housing 110 includes a housing 112 and a reflecting partition 114. The reflecting partition 114 separates the first light integration space S1 and the second light integration space S2. A part of the housing 112 and the reflecting partition 114 surround the first light integration space S1, and another part of the housing 112 and the reflecting partition 114 surround the second light integration space S2.

In the embodiment, through the light reflecting housing 110, the first illumination beam I1 is diffusely reflected in the first light integration space S1, and the second illumination beam I2 is diffusely reflected in the second light integration space S2. In other words, both the housing 112 and the reflecting partition 114 have diffuse reflection surfaces, which can diffusely reflect the first illumination beam I1 and the second illumination beam I2. Moreover, the first illumination beam I1 may not enter the second light integration space S2, and the second illumination beam I2 may not enter the first light integration space S1 either.

The lens plate 140 has a flat plate portion 142 and a first convex lens portion 144 respectively disposed at one end of the first light integration space S1 and one end of the second light integration space S2. The flat plate portion 142 is configured to lean against a first portion P1 of skin 50 of a subject, and a convex surface 145 of the first convex lens portion 144 is configured to press into a second portion P2 of the skin 50 of the subject. In an embodiment, the focal length of the first convex lens portion 144 is 2 mm, for example. The first illumination beam I1 penetrates the flat plate portion 142 and is then reflected by the first portion P1 of the skin 50 into a first reflected beam R1. The second illumination beam I2 penetrates the first convex lens portion 144 and is then reflected by the second portion P2 of the skin 50 into a second reflected beam R2. The first reflected beam R1 penetrates the flat plate portion 142 and is then transmitted to the first light sensor 150 through the first light integration space S1, and the second reflected beam R2 penetrates the first convex lens portion 144 and is then transmitted to the second light sensor 160 through the second light integration space S2.

In the embodiment, through the light reflecting housing 110, the first reflected beam R1 is also diffusely reflected in the first light integration space S1, and the second reflected beam R2 is diffusely reflected in the second light integration space S2. In other words, both the housing 112 and the reflecting partition 114 have diffuse reflection surfaces, which can diffusely reflect the first reflected beam R1 and the second reflected beam R2. Moreover, the first reflected beam R1 may not enter the second light integration space S2, and the second reflected beam R2 may not enter the first light integration space S1 either. With the light integration effect of the light reflecting housing 110, the light intensity of the first reflected beam R1 and the second reflected beam R2 respectively sensed by the first light sensor 150 and the second light sensor 160 can be effectively improved.

In the embodiment, the first light source module 120 includes a first light-emitting element 122, a second light-emitting element 124, and a third light-emitting element 126 (as shown in FIG. 3). The second light source module 130 includes a fourth light-emitting element 132, a fifth light-emitting element 134, and a sixth light-emitting element 136. The first light-emitting element 122 is configured to emit a first sub-illumination beam B1, the second light-emitting element 124 is configured to emit a second sub-illumination beam B2, and the third light-emitting element 126 is configured to emit a third sub-illumination beam B3. The fourth light-emitting element 132 is configured to emit a fourth sub-illumination beam B4, the fifth light-emitting element 134 is configured to emit a fifth sub-illumination beam B5, and the sixth light-emitting element 136 is configured to emit a sixth sub-illumination beam B6. The first sub-illumination beam B1 and the fourth sub-illumination beam B4 have a first wavelength, the second sub-illumination beam B2 and the fifth sub-illumination beam B5 have a second wavelength, and the third sub-illumination beam B3 and the sixth sub-illumination beam B6 have a third wavelength. The first sub-illumination beam B1, the second sub-illumination beam B2, and the third sub-illumination beam B3 form the first illumination beam I1, and the fourth sub-illumination beam B4, the fifth sub-illumination beam B5, and the sixth sub-illumination beam B6 form the second illumination beam I2.

In the embodiment, the first light-emitting element 122, the second light-emitting element 124, and the third light-emitting element 126 are configured to alternately emit the first sub-illumination beam B1, the second sub-illumination beam B2, and the third sub-illumination beam B3. The first portion P1 of the skin 50 alternately reflects the first sub-illumination beam B1, the second sub-illumination beam B2, and the third sub-illumination beam B3 respectively into a first sub-reflected beam RS1, a second sub-reflected beam RS2, and a third sub-reflected beam RS3. Moreover, the first light sensor 150 alternately senses the first sub-reflected beam RS1, the second sub-reflected beam RS2, and the third sub-reflected beam RS3 at different times.

The fourth light-emitting element 132, the fifth light-emitting element 134, and the sixth light-emitting element 136 are configured to alternately emit the fourth sub-illumination beam B4, the fifth sub-illumination beam B5, and the sixth sub-illumination beam B6. The second portion P2 of the skin 50 alternately reflects the fourth sub-illumination beam B4, the fifth sub-illumination beam B5, and the sixth sub-illumination beam B6 respectively into a fourth sub-reflected beam RS4, a fifth sub-reflected beam RS5, and a sixth sub-reflected beam RS6. Moreover, the second light sensor 160 alternately senses the fourth sub-reflected beam RS4, the fifth sub-reflected beam RS5, and the sixth sub-reflected beam RS6 at different times.

In the embodiment, the first light-emitting element 122, the second light-emitting element 124, the third light-emitting element 126, the fourth light-emitting element 132, the fifth light-emitting element 134, and the sixth light-emitting element 136 are light-emitting diodes, for example. However, in other embodiments, they can also be laser diodes or other light-emitting elements. Moreover, in the embodiment, the first light sensor 150 and the second light sensor 160 are photodiodes, for example. However, in other embodiments, they may also be other light sensors.

In the embodiment, the oxygenated hemoglobin and hemoglobin in the blood of the skin 50 of the subject have the same absorption coefficient for light with the second wavelength, and the absorption coefficient of the oxygenated hemoglobin and hemoglobin for lights with the first wavelength and the third wavelength shows an opposite trend along with the amount of the oxygen concentration. For example, the first wavelength is 740 nanometers, the second wavelength is 808 nanometers, and the third wavelength is 850 nanometers. These three wavelengths all belong to the infrared light band. Specifically, the propagation and traveling of light in biological tissues depends on the scattering coefficient of the tissues. Therefore, light-emitting elements with similar wavelengths are chosen so that the paths of these three wavelengths in the tissues are relatively the same. These wavelengths are chosen because oxygenated hemoglobin and hemoglobin have the same absorption coefficient for the central wavelength of the 808 nm light-emitting diode, the intensity of the reflected light at this wavelength may not change with the oxygen saturation concentration of hemoglobin and oxygenated hemoglobin, and only the changing amount of blood in the tissue may cause a change in the reflected light of 808 nanometers. The absorption coefficients of oxygenated hemoglobin and hemoglobin for 740 nm and 850 nm show an opposite trend along with amounts of the oxygen concentrations therein, so the oxygen concentration changes can have a higher resolution. The blood volume and oxygen concentration in the tissue can be easily quantified under the measurement of these three wavelengths, and the near-infrared light in this wavelength band is called the tissue window, because the absorption of substances in skin tissues other than blood is very small, more blood vessel information can be sensed, and it can also be more suitable for patients with dark skin. This is because most dark-skinned subcutaneous tissues usually make it difficult for doctors to determine the color change caused by the blood change after the finger presses the skin.

In the embodiment, the topical subcutaneous microcirculation detection device 100 further includes a controller 190 electrically connected to the first light source module 120, the second light source module 130, the first light sensor 150, and the second light sensor 160. Moreover, the topical subcutaneous microcirculation detection device 100 is configured to calculate the difference of absorbance caused by the blood of the second portion P2 of the skin 50 being squeezed by the convex surface 145 according to the difference between the light intensity of the first reflected beam R1 and the light intensity of the second reflected beam R2 sensed by the first light sensor 150 and the second light sensor 160. Moreover, the controller 190 can also calculate the blood oxygen concentration of the skin 50 according to the difference between the light intensity of the first reflected beam R1 and the light intensity of the second reflected beam R2.

Specifically, with the light intensity $R_{np}^{\lambda}$ (equivalent to the light intensity measured without pressing the skin 50) sensed by the first light sensor 150 and the light intensity $R_p^{\lambda}$ (equivalent to the light intensity measured by pressing the skin 50 through the convex surface 145 of the first convex lens portion 144) sensed by the second light sensor 160, the controller 190 can calculate the difference of absorbance $\Delta A_{Blood}^{\lambda}$ caused by the blood squeezed by the first convex lens portion 144, and the calculation method is as follows.

$$\Delta A_{Blood}^{\lambda} = \log \frac{R_p^{\lambda}}{R_{np}^{\lambda}} \quad \text{Formula (1)}$$

Since the first reflected beam R1 and the second reflected beam R2 each have three sub-beams with three different wavelengths, the light intensity $R_{np}^{\lambda_1}$ of the first sub-reflected beam RS1 measured by the first light sensor 150 and the light intensity $R_p^{\lambda_1}$ of the fourth sub-reflected beam RS4 measured by the second light sensor 160 respectively can be substituted into the $R_{np}^{\lambda}$ and $R_p^{\lambda}$ in the formula (1) to obtain the absorbance difference $\Delta A_{Blood}^{\lambda} = \Delta A_{Blood}^{\lambda_1}$ corresponding to the first wavelength. Similarly, the light intensity $R_{np}^{\lambda_2}$ of the second sub-reflected beam RS2 measured by the first light sensor 150 and the light intensity $R_p^{\lambda_2}$ of the fifth sub-reflected beam RS5 measured by the second light sensor 160 respectively can be substituted into the $R_{np}^{\lambda}$ and $R_p^{\lambda}$ in formula (1) to the absorbance difference $\Delta A_{Blood}^{\lambda} = \Delta A_{Blood}^{\lambda_2}$ corresponding to the second wavelength. Moreover, the light intensity $R_{np}^{\lambda_3}$ of the third sub-reflected beam RS3 measured by the first light sensor 150 and the light intensity $R_p^{\lambda_3}$ of the sixth sub-reflected beam RS6 measured by the second light sensor 160 respectively can be substituted into $R_{np}^{\lambda}$ and $R_p^{\lambda}$ in the formula (1) to obtain the absorbance difference $\Delta A_{Blood}^{\lambda} = \Delta A_{Blood}^{\lambda_3}$ corresponding to the third wavelength.

Then, the controller 190 can substitute the three absorbance differences $\Delta A_{Blood}^{\lambda}$ calculated by using the light intensities of the three different wavelengths into the modified Beer's law formula to obtain three formulae, and these three simultaneous equations are solved to obtain oxygenated hemoglobin concentration $l_{HbO2}$ and hemoglobin concentration bib. The modified Beer's law formula is as follows.

$$\Delta A_{Blood}^{\lambda} = a_{HbO2}^{\lambda} l_{HbO2} + a_{Hb}^{\lambda} l_{Hb} + s_t^{\lambda} l_s \quad \text{Formula (2)}$$

The modified Beer's law formula of formula (2) is used to quantify the contribution of oxygenated hemoglobin and hemoglobin. The original Beer's law is a basic tool to distinguish the absorbance of different chromophores in a translucent sample solution. Since biological tissues are usually opaque and have strong light scattering properties, baseline shifts are usually found in the tissue absorption spectrum. Therefore, a scattering term $s_t^{\lambda} l_s$ can be added to modify Beer's law formula to match the absorbance changes in opaque samples. In formula (2), $a_{HbO2}^{\lambda}$, $a_{Hb}^{\lambda}$, and $s_t^{\lambda}$ are constants, and after substituting the $\Delta A_{Blood}^{\lambda}$ values corresponding to the three different wavelengths into formula (2), three equations can be obtained. After solving them simultaneously, the three unknown numbers of the oxygenated hemoglobin concentration $l_{HbO2}$, hemoglobin concentration $l_{Hb}$, and the degree $l_s$ of influence of scattering can be solved.

After the controller 190 obtains the oxygenated hemoglobin concentration $l_{HbO2}$ and the hemoglobin concentration bib, the changed blood volume ΔBlood due to the pressing of the skin 50 pressed by the first convex lens portion 144 can be further obtained according to formula (3) as follows:

$$\Delta \text{Blood} = l_{HbO2} + l_{Hb} \quad \text{Formula (3)}$$

Moreover, the controller 190 can also calculate the blood oxygen saturation concentration $SBO_2\%$ of the tissue area of the pressed skin 50 according to the obtained oxygenated hemoglobin concentration $l_{HbO2}$, hemoglobin concentration bib, and formula (4) as follows.

$$SBO_2\% = [l_{HbO2}/(l_{HbO2} + l_{Hb})] \times 100\% \quad \text{Formula (4)}$$

With the calculation of formula (1) to formula (4) by the controller 190, the state of the topical subcutaneous microvascular circulation of the skin 50 generated by being pressed by the first convex lens portion 144 can be quantified, which can be used as the basis for the detection of initial pressure injury, the reliability of the detection result is higher than that of the skin blanching test observed with the naked eye, and the difficulty in observing the blanching of the skin due to the darker skin of the subject can be prevented.

Moreover, skin tissue has high scattering properties, so after light enters the tissue, the reflected light may radiate in all directions through the skin surface. To accurately collect the light reflection signals of all the skin 50 at the pressing and non-pressing positions and to make the two sides not to interfere with each other, in the embodiment, the light reflecting housing 110 is configured to form a small integrating space with one cavity and two chambers, which is placed above a special lens plate 140 to collect the light reflected by the respective skin 50 respectively. These two chambers (i.e., the first light integration space S1 and the second light integration space S2) each have the same special-made three near-infrared light-emitting elements with different wavelengths and a photodiode light sensor. These components are placed on the same plane to ensure that the light emitted by the light source does not directly enter the photodiode light sensor but is absorbed and then reflected by the tissue of the skin 50, and the light emitted by the light source can then be sensed.

In one embodiment, for example, the controller 190 is a central processing unit (CPU), a microprocessor, a digital signal processor (DSP), a programmable controller, a programmable logic device (PLD), other similar devices, or a combination thereof, and the disclosure is not limited thereto. Moreover, in one embodiment, each function of the controller 190 can be implemented as a plurality of program codes. These program codes are stored in a memory, and the controller 190 executes the program codes. Alternatively, in an embodiment, each function of the controller 190 may be implemented as one or more circuits. The disclosure does not limit using software or hardware to implement each function of the controller 190.

Figure 4:
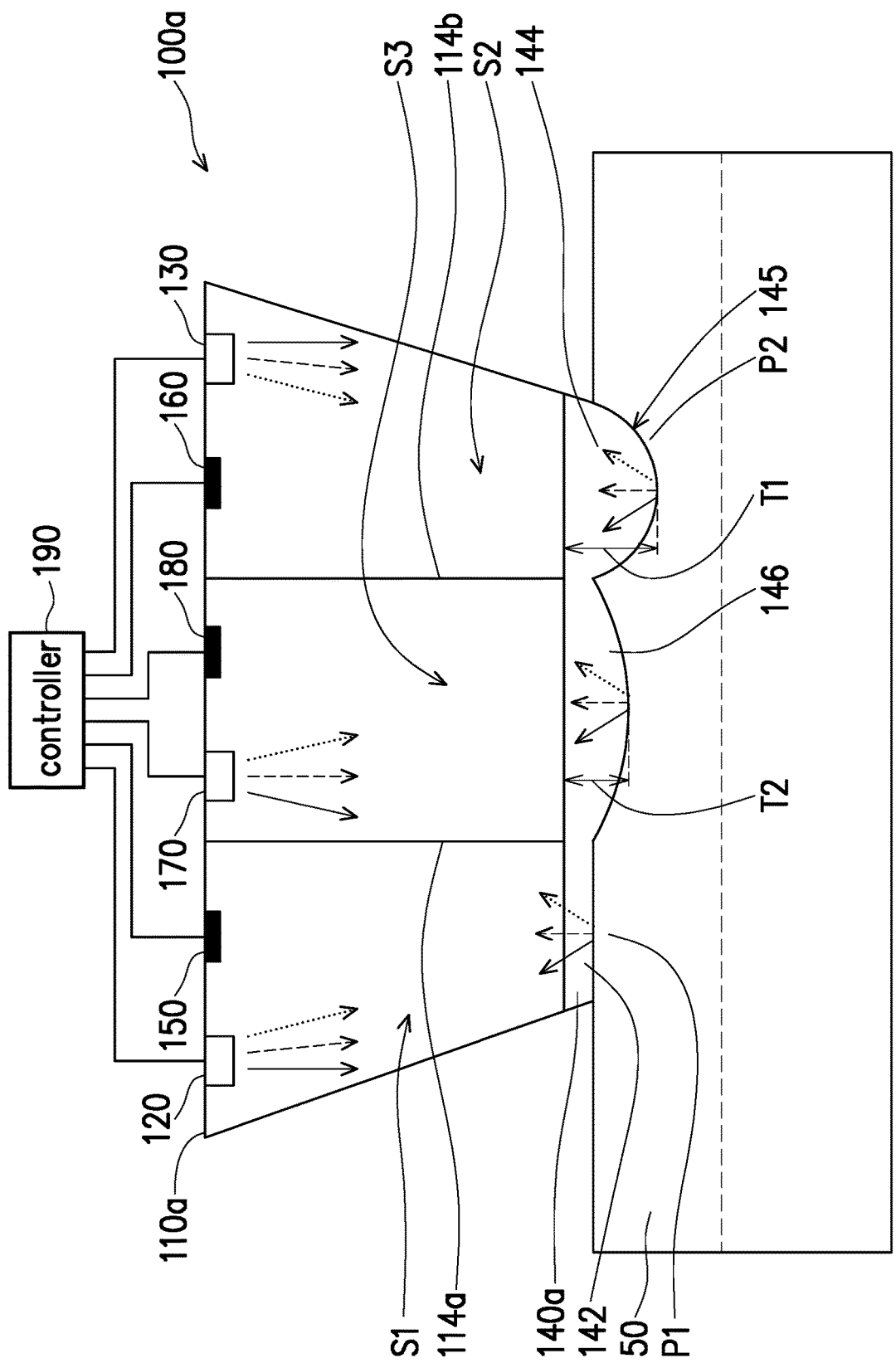
FIG. 4 is a schematic cross-sectional view of a topical subcutaneous microcirculation detection device according to another embodiment of the disclosure.

FIG. 4 is a schematic cross-sectional view of a topical subcutaneous microcirculation detection device according to another embodiment of the disclosure. Referring to FIG. 4, a topical subcutaneous microcirculation detection device 100a of the embodiment is similar to the topical subcutaneous microcirculation detection device 100 of FIG. 1, and the difference between the two is as follows. The topical subcutaneous microcirculation detection device 100a of the embodiment further includes a third light source module 170 and a third light sensor 180, and a lens plate 140a further has a second convex lens portion 146. The relative positional relationship of the third light source module 170, the third light sensor 180, and the second convex lens portion 146 is the same as the relative positional relationship of the second light source module 130, the second light sensor 160, and the first convex lens portion 144. However, a thickness T2 of the second convex lens portion 146 is different from a thickness T1 of the first convex lens portion 144. The third light source module 170 and the third light sensor 180 and their operation method can be the same as or similar to the operation method of the second light source module 130 and the second light sensor 160, they can also emit and detect three different types of wavelengths, the third light source module 170 and the third light sensor 180 are also electrically connected to the controller 190 so as to be controlled by the controller 190, and the controller 190 can calculate the value measured by the third light sensor 180.

The third light source module 170 and the third light sensor 180 may have a corresponding third light integration space S3 which is separated from the first light integration space S1 by the reflecting partition 114a of the light reflecting housing 110a and is separated from the second light integration space S2 by the reflecting partition 114b of the light reflecting housing 110a.

Due to the difference between the thicknesses of the second convex lens portion 146 and the first convex lens portion 144, different degrees of pressing can happen to the skin 50, and the state of the topical subcutaneous microvascular circulation can be measured more holistically and accurately. In other embodiments, the lens plate may have more convex lens portions with different thicknesses, and the topical subcutaneous microcirculation detection device can have more sets of light source modules and light sensors, by which 3 or more types of degrees of pressing happening to the skin are measured so that the state of the topical subcutaneous microvascular circulation can be measured more holistically and accurately.

In summary, in the topical subcutaneous microcirculation detection device of the embodiments of the disclosure, the lens plate having a flat plate portion and a first convex lens portion is configured to perform actions of no pressing and pressing on the skin, and the first light source module, the first light sensor, the second light source module, and the second light sensor are used for optical detection of the skin that is not pressed and the skin that is pressed, respectively. Accordingly, in the topical subcutaneous microcirculation detection device of the embodiments of the disclosure, a quantitative measurement of the topical subcutaneous microcirculation of subjects can be implemented.

What is claimed is:

1. A topical subcutaneous microcirculation detection device, comprising:

a first light source configured to emit a first illumination beam;

a second light source configured to emit a second illumination beam;

a lens plate comprising a flat plate portion and a first convex lens portion, wherein the flat plate portion is configured to lean against a first portion of skin of a subject, a convex surface of the first convex lens portion is configured to press into a second portion of the skin, the flat plate portion is disposed on a path of the first illumination beam and configured to allow the first illumination beam to penetrate through, the first portion of the skin is disposed on a path of the first illumination beam from the flat plate portion and configured to reflect the first illumination beam into a first reflected beam, the first convex portion is disposed on a path of the second illumination beam and configured to allow the second illumination beam to penetrate through, the second portion of the skin is disposed on a path of the second illumination beam from the first convex portion and configured to reflect the second illumination beam into a second reflected beam;

a first light sensor disposed on a path of the first reflected beam penetrating the flat plate portion;

a second light sensor disposed on a path of the second reflected beam penetrating the first convex lens portion; and a controller electrically connected to the first light source, the second light source, the first light sensor, and the second light sensor and configured to calculate a difference between absorbance of the first portion of the skin and absorbance of the second portion of the skin according to a difference between light intensity of the first reflected beam and light intensity of the second reflected beam sensed by the first light sensor and the second light sensor.

2. The topical subcutaneous microcirculation detection device according to claim 1, further comprising a light reflecting housing having a reflecting partition to separate a first light integration space and a second light integration space, wherein the first light source and the first light sensor are disposed in the first light integration space, and the second light source and the second light sensor are disposed in the second light integration space.

3. The topical subcutaneous microcirculation detection device according to claim 2, wherein the light reflecting housing is configured to diffusely reflect the first illumination beam and the first reflected beam in the first light integration space, and configured to diffusely reflect the second illumination beam and the second reflected beam in the second light integration space.

4. The topical subcutaneous microcirculation detection device according to claim 1, wherein the first light source comprises:
a first light emitter configured to emit a first sub-illumination beam;
a second light emitter configured to emit a second sub-illumination beam; and
a third light emitter configured to emit a third sub-illumination beam, wherein the second light source comprises:
a fourth light emitter configured to emit a fourth sub-illumination beam;
a fifth light emitter configured to emit a fifth sub-illumination beam; and
a sixth light emitter configured to emit a sixth sub-illumination beam,
wherein the first sub-illumination beam and the fourth sub-illumination beam have a first wavelength, the second sub-illumination beam and the fifth sub-illumination beam have a second wavelength, the third sub-illumination beam and the sixth sub-illumination beam have a third wavelength, the first sub-illumination beam, the second sub-illumination beam, and the third sub-illumination beam form the first illumination beam, and the fourth sub-illumination beam, the fifth sub-illumination beam, and the sixth sub-illumination beam form the second illumination beam.

5. The topical subcutaneous microcirculation detection device according to claim 4, wherein the first wavelength is 740 nanometers, the second wavelength is 808 nanometers, and the third wavelength is 850 nanometers.

6. The topical subcutaneous microcirculation detection device according to claim 4, wherein the first light emitter, the second light emitter, and the third light emitter are configured to alternately emit the first sub-illumination beam, the second sub-illumination beam, and the third sub-illumination beam; the first portion of the skin is configured to alternately reflect the first sub-illumination beam, the second sub-illumination beam, and the third sub-illumination beam into a first sub-reflected beam, a second sub-reflected beam, and a third sub-reflected beam, respectively; the first light sensor is configured to alternately sense the first sub-reflected beam, the second sub-reflected beam, and the third sub-reflected beam; the fourth light emitter, the fifth light emitter, and the sixth light emitter are configured to alternately emit the fourth sub-illumination beam, the fifth sub-illumination beam, and the sixth sub-illumination beam; the second portion of the skin is configured to alternately reflect the fourth sub-illumination beam, the fifth sub-illumination beam, and the sixth sub-illumination beam into a fourth sub-reflected beam, a fifth sub-reflected beam, and a sixth sub-reflected beam, respectively; and the second light sensor is configured to alternately sense the fourth sub-reflected beam, the fifth sub-reflected beam, and the sixth sub-reflected beam.

7. The topical subcutaneous microcirculation detection device according to claim 1, wherein the controller is configured to further calculate oxygen concentration of the blood of the skin according to the difference between the light intensity of the first reflected beam and the light intensity of the second reflected beam.

8. The topical subcutaneous microcirculation detection device according to claim 1, further comprising a third light source and a third light sensor, wherein the lens plate further comprises a second convex lens portion, and a positional relationship of the third light source, the third light sensor, and the second convex lens portion is the same as a positional relationship of the second light source, the second light sensor, and the first convex lens portion, but a thickness of the second convex lens portion is different from a thickness of the first convex lens portion.

9. A topical subcutaneous microcirculation detection device, comprising:
a light reflecting housing having a first light integration space and a second light integration space separated from each other;
a first light source disposed in the first light integration space and configured to emit a first illumination beam transmitted in the first light integration space;
a second light source disposed in the second light integration space and configured to emit a second illumination beam transmitted in the second light integration space;
a lens plate comprising a flat plate portion and a first convex lens portion, respectively disposed at one end of the first light integration space and one end of the second light integration space, wherein the flat plate portion is configured to lean against a first portion of skin of a subject, a convex surface of the first convex lens portion is configured to press into a second portion of the skin, the flat plate portion is disposed on a path of the first illumination beam and configured to allow the first illumination beam to penetrate through, the first portion of the skin is disposed on a path of the first illumination beam from the flat plate portion and configured to reflect the first illumination beam into a first reflected beam, the first convex portion is disposed on a path of the second illumination beam and configured to allow the second illumination beam to penetrate through, the second portion of the skin is disposed on a path of the second illumination beam from the first convex portion and configured to reflect the second illumination beam into a second reflected beam;
a first light sensor disposed on a path of the first reflected beam penetrating the flat plate portion and transmitted through the first light integration space;
a second light sensor disposed on a path of the second reflected beam penetrating the first convex lens portion and transmitted through the second light integration space; and
a controller electrically connected to the first light source, the second light source, the first light sensor, and the second light sensor and configured to calculate a difference between absorbance of the first portion of the skin and absorbance of the second portion of the skin according to a difference between light intensity of the first reflected beam and light intensity of the second reflected beam sensed by the first light sensor and the second light sensor.

10. The topical subcutaneous microcirculation detection device according to claim 9, wherein the light reflecting housing is configured to diffusely reflect the first illumination beam and the first reflected beam in the first light integration space, and configured to diffusely reflect the second illumination beam and the second reflected beam in the second light integration space.

11. The topical subcutaneous microcirculation detection device according to claim 9, wherein the first light source comprises:
   a first light emitter configured to emit a first sub-illumination beam;
   a second light emitter configured to emit a second sub-illumination beam; and
   a third light emitter configured to emit a third sub-illumination beam, wherein the second light source comprises:
   a fourth light emitter configured to emit a fourth sub-illumination beam;
   a fifth light emitter configured to emit a fifth sub-illumination beam; and
   a sixth light emitter configured to emit a sixth sub-illumination beam,
   wherein the first sub-illumination beam and the fourth sub-illumination beam have a first wavelength, the second sub-illumination beam and the fifth sub-illumination beam have a second wavelength, the third sub-illumination beam and the sixth sub-illumination beam have a third wavelength, the first sub-illumination beam, the second sub-illumination beam, and the third sub-illumination beam form the first illumination beam, and the fourth sub-illumination beam, the fifth sub-illumination beam, and the sixth sub-illumination beam form the second illumination beam.

12. The topical subcutaneous microcirculation detection device according to claim 11, wherein the first wavelength is 740 nanometers, the second wavelength is 808 nanometers, and the third wavelength is 850 nanometers.

13. The topical subcutaneous microcirculation detection device according to claim 11, wherein the first light emitter, the second light emitter, and the third light emitter are configured to alternately emit the first sub-illumination beam, the second sub-illumination beam, and the third sub-illumination beam; the first portion of the skin is configured to alternately reflect the first sub-illumination beam, the second sub-illumination beam, and the third sub-illumination beam into a first sub-reflected beam, a second sub-reflected beam, and a third sub-reflected beam, respectively; the first light sensor is configured to alternately sense the first sub-reflected beam, the second sub-reflected beam, and the third sub-reflected beam; the fourth light emitter, the fifth light emitter, and the sixth light emitter are configured to alternately emit the fourth sub-illumination beam, the fifth sub-illumination beam, and the sixth sub-illumination beam; the second portion of the skin is configured to alternately reflect the fourth sub-illumination beam, the fifth sub-illumination beam, and the sixth sub-illumination beam into a fourth sub-reflected beam, a fifth sub-reflected beam, and a sixth sub-reflected beam, respectively; and the second light sensor is configured to alternately sense the fourth sub-reflected beam, the fifth sub-reflected beam, and the sixth sub-reflected beam.

14. The topical subcutaneous microcirculation detection device according to claim 9, wherein the controller is configured to further calculate oxygen concentration of the blood of the skin according to the difference between the light intensity of the first reflected beam and the light intensity of the second reflected beam.

15. The topical subcutaneous microcirculation detection device according to claim 9, further comprising a third light source and a third light sensor, wherein the lens plate further comprises a second convex lens portion, and a positional relationship of the third light source, the third light sensor, and the second convex lens portion is the same as a positional relationship of the second light source, the second light sensor, and the first convex lens portion, but a thickness of the second convex lens portion is different from a thickness of the first convex lens portion.

* * * * *